(12) United States Patent
Lee et al.

(10) Patent No.: US 8,722,880 B2
(45) Date of Patent: May 13, 2014

(54) METHOD FOR PREPARING 42-(DIMETHYLPHOSPHINATE) RAPAMYCIN

(71) Applicant: Chunghwa Chemical Synthesis & Biotech Co. Ltd., New Taipei (TW)

(72) Inventors: Kwang-Chung Lee, New Taipei (TW); Yen-Shih Tung, New Taipei (TW); Tzu-Ai Lee, New Taipei (TW); Yu-Hsuan Shih, New Taipei (TW)

(73) Assignee: Chunghwa Chemical Synthesis & Biotech Co., Ltd., New Taipei (TW)

( * ) Notice: Subject to any disclaimer, the term of this patent is extended or adjusted under 35 U.S.C. 154(b) by 0 days.

(21) Appl. No.: 13/967,597

(22) Filed: Aug. 15, 2013

(65) Prior Publication Data
US 2014/0058081 A1    Feb. 27, 2014

(30) Foreign Application Priority Data

Aug. 22, 2012 (TW) .............................. 101130353 A

(51) Int. Cl.
*C07D 491/06* (2006.01)
(52) U.S. Cl.
USPC .......................................... 540/456

(58) Field of Classification Search
USPC .......................................... 540/456
See application file for complete search history.

(56) References Cited

U.S. PATENT DOCUMENTS 7,091,213 B2    8/2006    Metcalf, III et al.

*Primary Examiner* — Bruck Kifle
(74) *Attorney, Agent, or Firm* — Muncy, Geissler, Olds & Lowe, P.C.

(57) ABSTRACT

A method for preparing 42-(dimethylphosphinate) Rapamycin (Ridaforolimus) (I) is provided, which has advantages of high conversion rate and no 31,42-bis(dimethyl phosphinate) Rapamycin (III) generated. In the method of the present invention, Rapamycin (II) is firstly reacted with triethyl chlorosilane in a base condition to form 31,42-bis(triethylsilylether) Rapamycin (IV-b), followed by a selective deprotection process to obtain 31-triethylsilylether Rapamycin (V-b). Next, a phosphorylation reaction is performed by using dimethylphosphinic chloride under a base solution to obtain a crude product. Finally, a deprotection reaction is performed in a diluted sulfuric acid solution to obtain a crude product of Ridaforolimus (I). Since the conversion rate of each step of the method of the present invention is higher than 98%, it indicates that the method of the present invention is suitable for industrial production.

8 Claims, No Drawings

METHOD FOR PREPARING 42-(DIMETHYLPHOSPHINATE) RAPAMYCIN

CROSS REFERENCE TO RELATED APPLICATION

This application claims the benefits of the Taiwan Patent Application Serial Number 101130353, filed on Aug. 22, 2012, the subject matter of which is incorporated herein by reference.

BACKGROUND OF THE INVENTION

1. Field of the Invention

The present invention relates to a novel method for preparing 42-(dimethylphosphinate) Rapamycin (Ridaforolimus) represented by the following formula I:

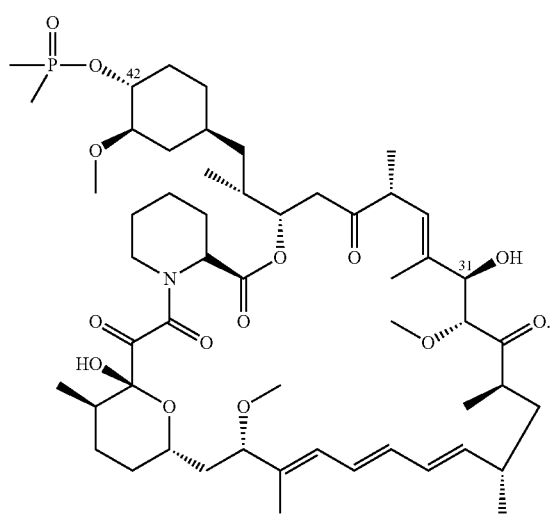

2. Description of Related Art

The mammalian target of Rapamycin (mTOR) is known as a mechanistic target of Rapamycin (II), which is found in the studies of Rapamycin. On the other hand, 42-(dimethylphosphinate) Rapamycin (Ridaforolimus) (I) is a derivative of Rapamycin (II), which is also a kind of mTOR inhibitor. Ridaforolimus (I) can inhibit cell division and possibly lead to tumor cell death. Hence, there are many studies related to solid tumor treatments and blood cancer treatments using Ridaforolimus (I). In addition, in 2011, Merck also applied a certification of this compound against soft tissue and bone cancer.

U.S. Pat. No. 7,091,213 discloses a process for preparing 42-(dimethylphosphinate) Rapamycin (Ridaforolimus) (I), and the process thereof is shown in the following Scheme I.

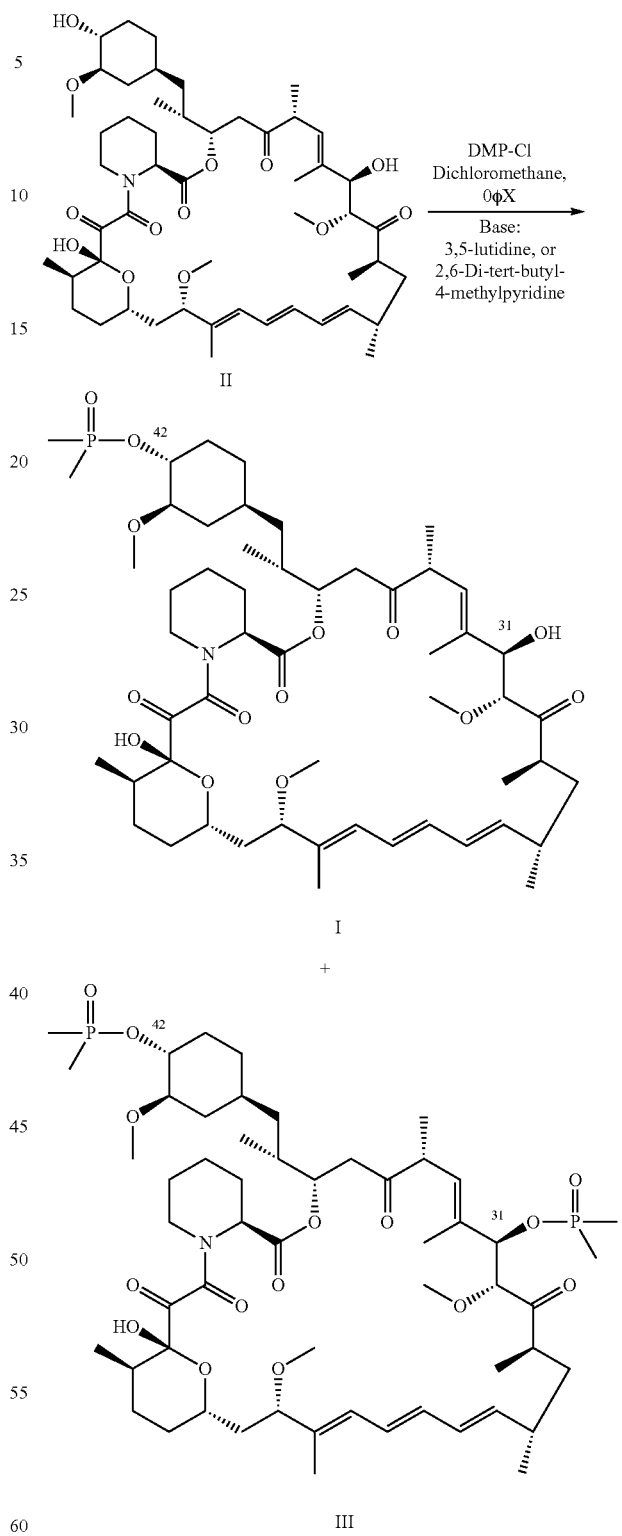

In this process, a solution of Rapamycin (II) in dichloromethane (DCM) was respectively added with 2,6-di-tert-butyl-4-methylpyridine or 3,5-lutidine as a base, and followed by the addition of a solution of dimethylphosphinic chloride (DMP-Cl) to perform a phosphorylation reaction at 0° C., under a stream of $N_{2(g)}$. The crude product was purified by flash chromatography (eluted with MeOH/DCM/EtOAc/hexane=1:10:3:3) to provide 42-(dimethyl-phosphinate) Rapamycin (Ridaforolimus) (I), which is a phosphorylated compound at 42-hydroxyl position of Rapamycin (II). In addition, this patent also disclosed a side product of 31,42-bis(dimethyl phosphinate) Rapamycin (III), which is a phosphorylated compound at both 31-hydroxyl position and 42-hydroxyl position of Rapamycin (II).

SUMMARY OF THE INVENTION

U.S. Pat. No. 7,091,213 discloses a process for preparing 42-(dimethylphosphinate) Rapamycin (Ridaforolimus) (I), and the process thereof is shown in Scheme I. According to one example thereof, to a cooled (0° C.) solution of Rapamycin (II) (0.1 g) in dichloromethane (DCM) 2,6-di-tert-butyl-4-methylpyridine (7.5 molar equivalents) was added as a base, under a stream of $N_{2(g)}$, and followed immediately by addition of a solution of dimethylphosphinic chloride (DMP-Cl) (5 molar equivalents) to perform a phosphorylation reaction for 3.5 h. The crude product was purified by flash chromatography (eluted with MeOH/DCM/EtOAc/hexane=1:10:3:3) to provide 0.092 g of 42-(dimethylphosphinate) Rapamycin (Ridaforolimus) (I). According to another example thereof, the phosphorylation reaction was achieved by reacting Rapamycin (II) with 3,5-lutidine (2.2 molar equivalents, as a base) and dimethylphosphinic chloride (DMP-Cl) (2.0 molar equivalents). However, the conversion rate and the yield thereof did not disclosed therein. Hence, the present inventor prepared Ridaforolimus (I) using Rapamycin (II) as a starting material based on the aforementioned examples. When 2,6-di-tert-butyl-4-methylpyridine (7.5 molar equivalents) was used as a base and dimethylphosphinic chloride (DMP-Cl) (5 molar equivalents) was used to perform the phosphorylation reaction at 0° C. for 3.5 h, under a stream of $N_{2(g)}$, the conversion rate thereof was more than 98%. However, when the crude product of Ridaforolimus (I) was analyzed by HPLC using the following system A, the HPLC analysis data indicated that a side product 31,42-bis(dimethyl phosphinate) Rapamycin (III) was generated, and a ratio of Ridaforolimus (I) and 31,42-bis(dimethyl phosphinate) Rapamycin (III) was 96.8:3.2. When 3,5-lutidine (2.2 molar equivalents) was used as a base and dimethylphosphinic chloride (DMP-Cl) (2.0 molar equivalents) was used to perform the phosphorylation reaction at 0° C. for 1.5 h, under a stream of $N_{2(g)}$, the conversion rate thereof was only 8.48%. In addition, the side product 31,42-bis(dimethyl phosphinate) Rapamycin (III) was also observed, and the ratio of Ridaforolimus (I) and 31,42-bis(dimethyl phosphinate) Rapamycin (III) was 96.92:2.92. When the amount of dimethylphosphinic chloride (DMP-Cl) was increased to 5.0 molar equivalents to perform the phosphorylation reaction under the same condition, there was 5.75% of the starting material unreacted, the conversion rate thereof was 94.25%, and the ratio of Ridaforolimus (I) and 31,42-bis(dimethyl phosphinate) Rapamycin (III) was 98.87:1.14.

The conditions or the analytical system of HPLC is illustrated in the following description:
System A for HPLC analysis
Column: YMC Hydrosphere C18 column, 250×4.6 mm I.D. S-3 μm, 12 nm;
Column temperature: 45° C.;
Eluent A: Acetonitrile;
Eluent B: 0.02M Ammonium formate solution, wherein the pH of the ammonium formate solution was adjusted to 4.0 with formic acid;

Gradient program:

| Time (min) | Eluent A (%) | Eluent B (%) |
|---|---|---|
| 0 | 60 | 40 |
| 20 | 60 | 40 |
| 30 | 95 | 5 |
| 40 | 95 | 5 |
| 45 | 60 | 40 |
| 55 | 60 | 40 |

Relative retention time (RRT): RRT of compound VI-a is 1.0, that of compound V-a is 0.958, that of compound I is 0.756, and that of compound III is 0.595.

The results of the aforementioned experiments performed by the present inventor confirmed that the conversion rate thereof was more than 98% only when using 2,6-di-tert-butyl-4-methylpyridine as a base. In this experiment, 7.5 molar equivalents of 2,6-di-tert-butyl-4-methylpyridine with high valence and 5 molar equivalents of dimethylphosphinic chloride have to be used to achieve the high conversion rate. However, the generated side product of 31,42-bis(dimethyl phosphinate) Rapamycin (III) may increase the difficulty of the sequential purification. On the other hand, in the experiment by using 3,5-lutidin as a base, less than 10% of the conversion rate can be achieved, and the side product of 31,42-bis(dimethyl phosphinate) Rapamycin (III) was also generated. Although the conversion rate can be improved to 94.25% by increasing the amount of dimethylphosphinic chloride (DMP-Cl) to 5.0 molar equivalents, the generated side product of 31,42-bis(dimethyl phosphinate) Rapamycin (III) still increases the difficulty of the sequential purification. Hence, the present invention provides a method for preparing 42-(dimethylphosphinate) Rapamycin (Ridaforolimus) (I) with high conversion rate without generating 31,42-bis(dimethyl phosphinate) Rapamycin (III).

The method for preparing 42-(dimethylphosphinate) Rapamycin (Ridaforolimus) (I) of the present invention comprises the following steps:

(a) reacting Rapamycin of the following formula II with a silane compound in a first basic condition to obtain a compound of the following formula IV:

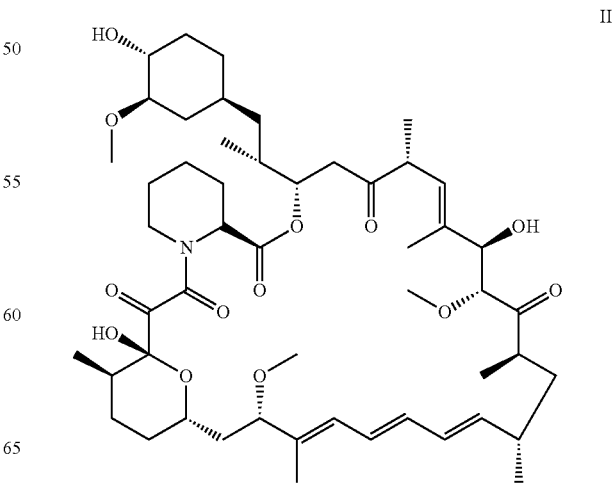

-continued

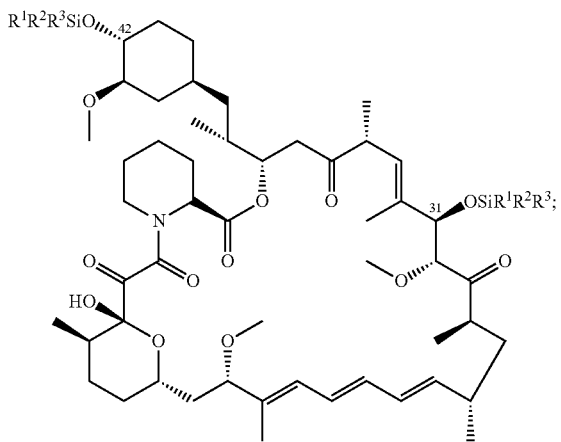

IV (b) deprotecting the compound of the formula IV in a first acid condition to obtain a compound of the following formula V:

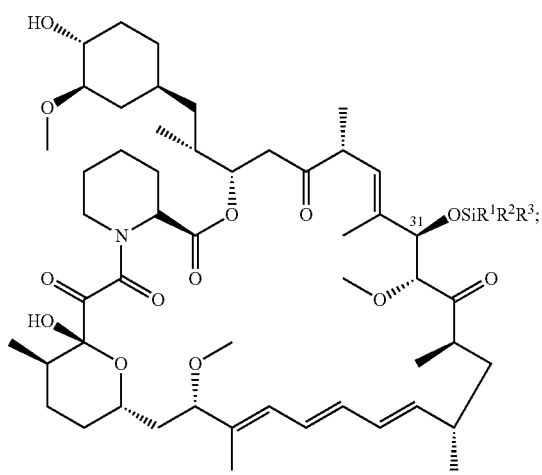

V (c) reacting the compound of the formula V with Dimethylphosphinic chloride in a second basic condition to perform a phosphorylation reaction to obtain a compound of the following formula VI:

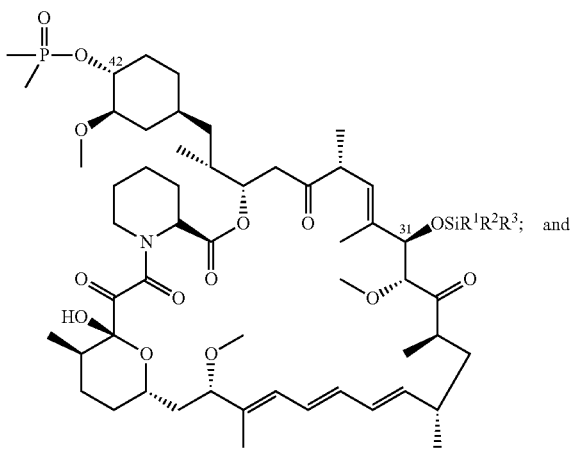

VI and (d) hydrolyzing the compound of the formula VI in a second acid condition to obtain Ridaforolimus of the formula I.

Herein, each $R^1$, $R^2$ and $R^3$ is independently H, $C_{1-6}$ linear alkyl, benzyl, phenyl, or p-methylbenzyl, with the proviso that all $R^1$, $R^2$ and $R^3$ are not H. Preferably, each $R^1$, $R^2$ and $R^3$ is independently H or $C_{1-6}$ linear alkyl. More preferably, each $R^1$, $R^2$ and $R^3$ is independently methyl or ethyl. Most preferably, all the $R^1$, $R^2$ and $R^3$ are methyl or ethyl.

In the method of the present invention, the silane compound used in the step (b) can be represented by the following formula VII:

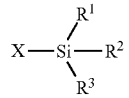

VII wherein each $R^1$, $R^2$ and $R^3$ is independently H, $C_{1-6}$ linear alkyl, benzyl, phenyl, or p-methylbenzyl, with the proviso that all $R^1$, $R^2$ and $R^3$ are not H, and X is Cl or —$OSO_2CFF_3$. Preferably, each $R^1$, $R^2$ and $R^3$ is independently H or $C_{1-6}$ linear alkyl. More preferably, each $R^1$, $R^2$ and $R^3$ is independently methyl or ethyl. Most preferably all the $R^1$, $R^2$ and $R^3$ are methyl or ethyl.

In addition, in the method of the present invention, an acid used in the first acid condition of the step (b) is not particularly limited, and can be hydrogen chloride, acetic acid, sulfuric acid, trifluoroacetic acid, hydrofluoric acid, or a combination thereof.

Furthermore, in the method of the present invention, a base used in the second basic condition of the step (c) is 2,6-di-tert-butyl-4-methyl pyridine, 3,5-lutidine, 2,6-lutidine, 2,4-lutidine, 2,3-lutidine, 2,5-lutidine, 3,4-lutidine, pyridine, 4-dimethylaminopyridine (DMAP), or a combination thereof. Preferably, the base is 2,6-di-tert-butyl-4-methyl pyridine, 3,5-lutidine or 2,6-lutidine. More preferably, the base is 2,6-di-tert-butyl-4-methylpyridine, or 3,5-lutidine.

In the method of the present invention, an acid used in the second acid condition of the step (d) is not particularly limited, and can be hydrogen chloride, acetic acid, sulfuric acid, tetrabutylammonium fluoride, trifluoroacetic acid, hydrofluoric acid, or a combination thereof. Preferably, the acid is sulfuric acid.

In the method of the present invention, the steps (a)-(d) are performed in a solvent. The solvent is not particularly limited, as long as the solvent does not react with the reacting materials and can stabilize the reaction materials and/or facilitate the reaction. Examples of the solvent comprise: tetrahydrofuran, dichloromethane, acetonitrile, ethyl acetate, dimethylformamide, and water. In the step (b) of the present invention, the solvent used in the first acid condition can be at least one selected from the group consisting of tetrahydrofuran, dichloromethane, acetonitrile, ethyl acetate, dimethylformamide, and water. In the step (c) of the present invention, the solvent used in the second basic condition can be at least one selected from the group consisting of tetrahydrofuran, dichloromethane, acetonitrile, and dimethylformamide. In the step (d) of the present invention, the solvent used in the second acid condition can be at least one selected from the group consisting of tetrahydrofuran, dichloromethane, acetonitrile, ethyl acetate, dimethylformamide, and water.

The process of the present invention is shown in the following Scheme II.

[Scheme II]

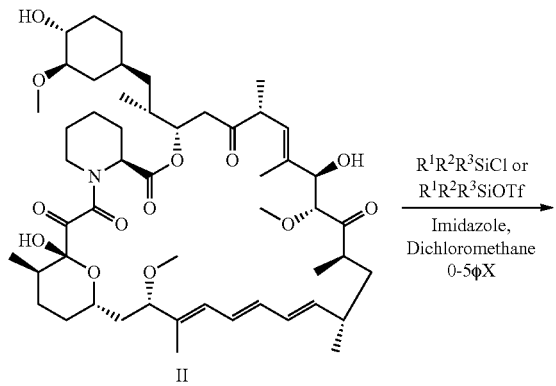

II

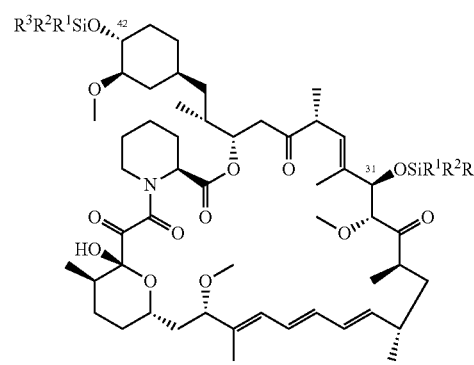

IV
IV-a: $R^1 = R^2 = R^3 = CH_3$
IV-b: $R^1 = R^2 = R^3 = CH_2CH_3$

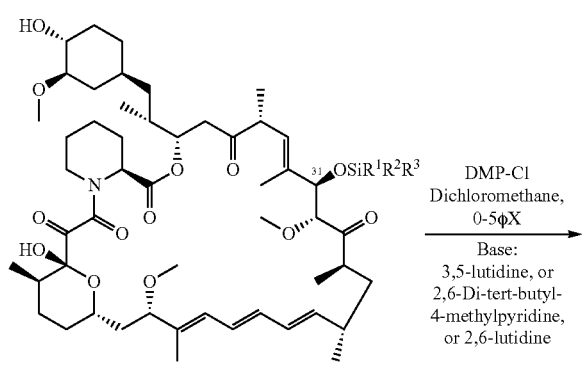

V
V-a: $R^1 = R^2 = R^3 = CH_3$
V-b: $R^1 = R^2 = R^3 = CH_2CH_3$

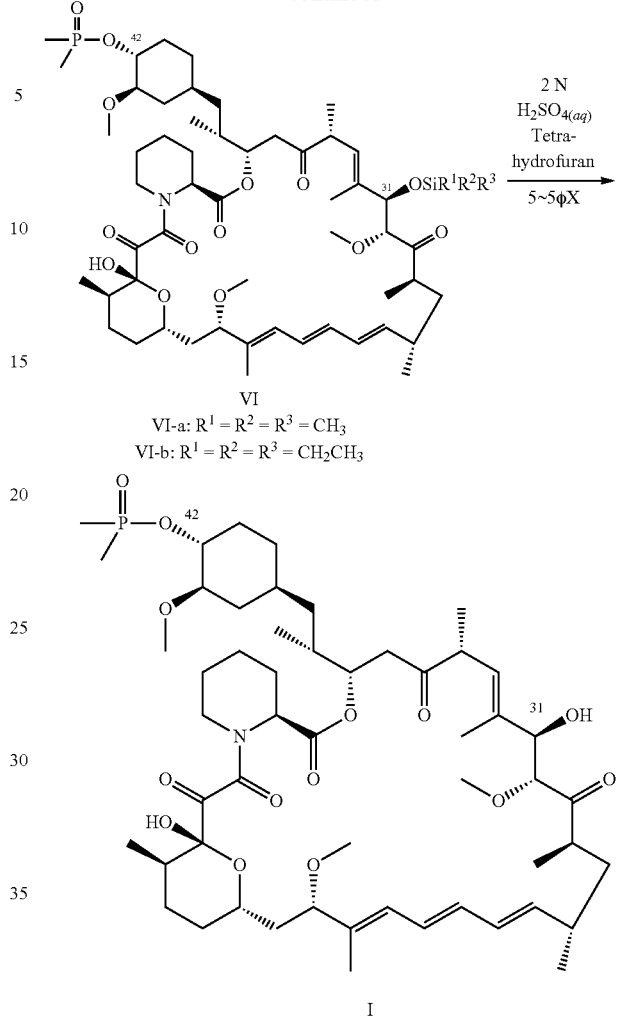

VI
VI-a: $R^1 = R^2 = R^3 = CH_3$
VI-b: $R^1 = R^2 = R^3 = CH_2CH_3$

I

In the step (a) and the step (b) of the method of the present invention, Rapamycin (i.e. the compound of the formula II) is used as a starting material, which is reacted with a silane compound such as $R^1R^2R^3SiCl$ and $R^1R^2R^3SiOSO_2CF_3$ ($R^1R^2R^3SiOTf$) under a base condition (for example, imidazole) to obtain the compound of the formula IV (31,42-bis(trialkylsilylether) Rapamycin). Then, the compound of the formula IV is deprotected in an acid condition to obtain the compound of the formula V (31-trialkylsilylether Rapamycin).

In the present invention, Rapamycin (II) is firstly reacted with triethyl chlorosilane (($CH_2CH_3)_3SiCl$) to form 31,42-bis(triethylsilylether) Rapamycin (IV-b), and then the compound IV-b is selectively deprotected in an ethyl acetate solution (EtOAc) to obtain 31-triethylsilylether Rapamycin (V-b). The conversion rate of the aforementioned two steps is higher than 98%, and the total yield thereof is higher than 93%.

On the other hand, Rapamycin (II) can be firstly reacted with trimethyl chlorosilane (($CH_3)_3SiCl$) to form 31,42-bis(trimethylsilylether) Rapamycin (IV-a), and then the compound IV-a is selectively deprotected to obtain 31-trimethylsilylether Rapamycin (V-a). When 2.5 g of Rapamycin (II) is used, 2.758 g of 31-trimethylsilylether Rapamycin (V-a) can be obtained. The HPLC analysis result indicates that the product contains 94.5% (area %) of 31-trimethylsilylether Rapamycin (V-a) and 5.5% of Rapamycin (II).

In the step (c) of the method of the present invention, in one aspect of 31-triethylsilylether Rapamycin (V-b), the compound V-b is reacted with Dimethylphosphinic chloride (DMP-Cl) in a solvent (for example, dichloromethane) by using a base such as 3,5-lutidine, 2,6-Di-tert-butyl-4-methylpyridine or 2,6-lutidine (in the following Table 1, the amount, of the base is 2 molar equivalents) at 0° C., under a stream of $N_{2(g)}$. The phosphorylation reaction can be monitored with HPLC using the aforementioned system A. The conversion rate of the obtained 42-(dimethylphosphinate)-31-triethylsilylether Rapamycin (VI-b) to the starting material is presented in the following Table 1.

TABLE 1

Conversion rate of the phosphorylation reaction by using different base and DMP-Cl with different amount

| Ex. | Base | DMP-Cl (molar equivalents) | Reaction time (hr) | Conversion rate |
|---|---|---|---|---|
| 1 | 3,5-lutidine | 3 | 2 | 90% |
| 2 | 3,5-lutidine | 4 | 2 | >98% |
| 3 | 2,6-Di-tert-butyl-4-methyl pyridine | 3 | 3 | <90% |
| 4 | 2,6-Di-tert-butyl-4-methyl pyridine | 4 | 3 | >98% |
| 5 | 2,6-lutidine | 3 | 1.5 | 46% |
| 6 | 2,6-lutidine | 4 | 1.5 | 62% |

As shown in Examples 1-2 of Table 1, when 3 or 4 molar equivalents of Dimethylphosphinic chloride is reacted with 31-triethylsilylether Rapamycin (V-b) under a base condition using 2.2 molar equivalents of 3,5-lutidine, the conversion rate of Example 1 using 3 molar equivalents of Dimethylphosphinic chloride is only 90%, but that of Example 2 using 4 molar equivalents of Dimethylphosphinic chloride can be as high as 98%. This result indicate that high conversion rate can be obtained and no side product of 31,42-bis(dimethyl phosphinate) Rapamycin (III) is generated by using the method of the present invention.

Furthermore, as shown in Examples 3-4 of Table 1, when 3 or 4 molar equivalents of Dimethylphosphinic chloride is reacted with 31-triethylsilylether Rapamycin (V-b) under a base condition using 2.2 molar equivalents of 2,6-Di-tert-butyl-4-methylpyridine, the conversion rate of Example 3 using 3 molar equivalents of Dimethylphosphinic chloride is only <90%, but that of Example 4 using 4 molar equivalents of Dimethylphosphinic chloride can be as high as 98%. In addition, when 375 mg of 31-triethylsilylether Rapamycin (V-b) is reacted with Dimethylphosphinic chloride in dichloromethane, the amount and the purity of the obtained crude product of 42-(dimethylphosphinate)-31-triethylsilylether Rapamycin (VI-b) are respectively 0.43 g and 96.66%, and no side product of 31,42-bis(dimethyl phosphinate) Rapamycin (III) is generated. This result indicates that high conversion rate can be achieved by using the method of the present invention.

In addition, as shown in Examples 5-6 of Table 1, when 3 or 4 molar equivalents of Dimethylphosphinic chloride is reacted with 31-triethylsilylether Rapamycin (V-b) under a base condition using 2.2 molar equivalents of 2,6-lutidine, the conversion rate of Examples 5-6 is respectively 46% and 62%, and there is no side product of 31,42-bis(dimethyl phosphinate) Rapamycin (III) generated. Although the conversion rate of Example 6 using 4 molar equivalents of Dimethylphosphinic chloride is only 62%, which is much lower than that shown in Examples 1-4, there is still no side product of 31,42-bis(dimethyl phosphinate) Rapamycin (III) generated.

As shown in Table 1, when 31-triethylsilylether Rapamycin (V-b) used as a material to react with 4 molar equivalents of Dimethylphosphinic chloride, the starting material can be totally transferred into the products even though the using amount of the base such as 2,6-Di-tert-butyl-4-methylpyridine and 3,5-lutidine is only 2.2 molar equivalents. In addition, not only high conversion rate can be achieved, but also no side product of 31,42-bis(dimethyl phosphinate) Rapamycin (III) is generated by using the method of the present invention. Hence, the present invention selects 3,5-lutidine, which is a cheap base, as a base for the phosphorylation reaction. When 1.0 g or 2.0 g of 31-triethylsilylether Rapamycin (V-b) is respectively reacted with 4 molar equivalents of Dimethylphosphinic chloride, both the conversion rate thereof is more than 98%. This result indicates that the reaction performed in the method of the present invention has reproducibility and feasibility. In addition, the amount and the purity of the obtained crude product of 42-(dimethylphosphinate)-31-triethylsilylether Rapamycin (VI-b) are respectively 1.17 g and 97.56% when using 1.0 g of the compound V-b, and 2.312 g and 97.01% when using 2.0 g of the compound V-b. This result indicates that the reaction performed in the method of the present invention has high conversion rate, so it is very suitable for industrial production.

On the other hand, in another aspect of 31-trimethylsilylether Rapamycin (V-a), when 300 mg of the compound V-a is reacted with 3 or 4 molar equivalents of Dimethylphosphinic chloride (DMP-Cl) in a solvent (for example, dichloromethane) under a base condition containing 2.2 molar equivalents of 3,5-lutidine, 314 mg of the crude product of 42-(dimethylphosphinate) Rapamycin (Ridaforolimus) (I) can be obtained. The HPLC analysis data indicate that the crude product contained 81.03% (area %) of 42-(dimethylphosphinate) Rapamycin (Ridaforolimus) (I), 5.14% of Rapamycin (II), 0.54% of 31,42-bis(dimethyl phosphinate) Rapamycin (III), and 2.5% of 42-(dimethylphosphinate)-31-trimethylsilylether Rapamycin (VI-a). This process also has high conversion rate, and the final product of 42-(dimethylphosphinate) Rapamycin (Ridaforolimus) (I) can be obtained without performing the hydrolysis process.

In the step (d) of the method of the present invention, 42-(dimethylphosphinate)-31-triethylsilylether Rapamycin (VI-b) is deprotected in a solvent (for example, tetrahydrofuran) at 0° C. by using a diluted sulfuric acid solution. The result indicates that high conversion rate (>98%) can be achieved in this step. In the step (c) of the method of the present invention, when 1.0 g or 2.0 g of the intermediate, 31-triethylsilylether Rapamycin (V-b) is phosphorylated, a crude product of 42-(dimethylphosphinate)-31-triethylsilylether Rapamycin (VI-b) can be obtained (weight=1.17 g, purity=97.56%; and weight=2.312 g, purity=97.01%). In the step (d) of the present invention, when the crude product of the compound V-b is deprotected, a crude product of 42-(dimethylphosphinate) Rapamycin (Ridathrolimus) (I) can be obtained (weight=1.13 g, purity=95.78%; and weight=2.34 g, purity=96.66%). These results indicate that the reaction performed in the method of the present invention has high conversion rate, so it is very suitable for industrial production. In addition, when the crude product of 42-(dimethylphosphinate) Rapamycin (Ridaforolimus) (I) (weight=1.13 g, purity=95.78%) prepared from 1 g of 31-triethylsilylether Rapamycin (V-b) is further purified by silica gel chromatography (eluted with MeOH/DCM/EtOAc/hexane=1:10:3:3), only 0.35 g of 42-(dimethylphosphinate) Rapamycin (Ridaforolimus) (I) (purity 96.62%) can be obtained. This result indicates that 42-(dimethylphosphinate) Rapamycin (Ridaforolimus) (I) may be lost when it stays in an eluent containing methanol for a predetermined period. However, when the crude product of 42-(dimethylphosphinate) Rapamycin (Ridaforolimus) (1) (weight=2.34 g, purity=96.66%) prepared from 2 g of 31-triethylsilylether Rapamycin (V-b) is further purified by reverse C-18 silica gel chromatography (eluted with acetonitrile: 0.02 M ammonium formate solution=6:4, wherein the pH of the ammonium formate solution was adjusted to 4.0 with formic acid), 1.84 g of 42-(dimethylphosphinate) Rapamycin (Ridaforolimus) (I) (purity>99.5% and yield=95.55% based on 2 g of 31-triethylsilylether Rapamycin (V-b)) can be obtained.

Each reaction performed in each step of the method of the present invention shows high conversion rate, and the sequential purification processes is very simple. In addition, even though less amount of 3,5-lutidine, which is a cheap base, is used in the phosphorylation reaction, high conversion rate still can be achieved and no side product of 31,42-bis(dimethyl phosphinate) Rapamycin (III) is generated. This result indicates that the method of the present invention is better than the conventional method and the separation or the purification process used in the present invention is easier than those used in the conventional method. Hence, the method of the present invention is very suitable for industrial production.

With regard to the structure determination of 42-(dimethylphosphinate) Rapamycin (Ridaforolimus) (I), $^1$H-NMR, $^{31}$P-NMR and MS data are consistent with those known in the art. Hence, 42-(dimethylphosphinate). Rapamycin (Ridaforolimus) (I) indeed can be obtained by using the method of the present invention.

Other objects, advantages, and novel features of the invention will become more apparent from the following detailed description when taken in conjunction with the accompanying drawings.

DETAILED DESCRIPTION OF THE PREFERRED EMBODIMENT

The following embodiments are used to describe the method of the present invention, but the scope of the present invention is not limited thereto.

Example 1

Preparation of 31-triethylsilylether Rapamycin (V-b)

To a flask containing Rapamycin (II) (10.0 g, 10.94 mmole) was added dichloromethane (60 mL). The resulting solution was cooled to 0-5° C., and then imidazole (3.0 g, 44.07 mmole) was added therein. After the resulting solution was stirred to dissolve the added imidazole completely, triethyl chlorosilane (6.1 g, 40.47 mmole) was added therein dropwise. Then, the resulting solution was stirred at 0-5° C. for 3 h, followed by filtration at room temperature. The filter cake was washed with ethyl acetate (200 mL), and then to the filtrate was added ethyl acetate (200 mL). After the filtrate was successively washed with water (2×100 mL) and a NaCl saturated solution (100 mL), the organic layer was dried over anhydrous sodium sulfate and concentrated to obtain yellow oil 31,42-bis(triethylsilylether) Rapamycin (IV-b). To 31,42-bis(triethylsilylether) Rapamycin (IV-b) was added tetrahydrofuran (32 mL). The resulting solution was cooled to 0-5° C., and then a mixture of acetic acid (98 mL) and water (52 mL) was added therein. The reaction solution was stirred at a temperature below 5° C. for 2.5 h, followed by adding ethyl acetate (300 mL). Then, a NaHCO$_3$ saturated solution was added into the reaction solution dropwise ate a temperature below 10° C. until the pH thereof was 7.0-7.5. After the organic layer and the aqueous layer were separated, the organic layer was collected, and the aqueous layer was extracted with ethyl acetate (300 mL). The overall organic layer was successively washed with water (2×150 mL) and a NaCl saturated solution (100 mL), dried over anhydrous sodium sulfate and concentrated to obtain a yellow oil crude product of 31-triethylsilylether Rapamycin (V-b) (17.1 g). The crude product was purified by chromatography (eluted with ethyl acetate:hexane=2:1) to provide a white solid of 31-triethylsilylether Rapamycin (V-b) (10.44 g). The yield thereof was 93%.

Example 2

Preparation of 31-trimethylsilylether Rapamycin (V-a)

To a flask containing Rapamycin (II) (2.5 g, 2.73 mmole) was added ethyl acetate (75 mL). The resulting solution was cooled to 0-5° C., and then imidazole (0.75 g, 10.93 mmole) was added therein. After the resulting solution was stirred to dissolve the added imidazole completely, trimethyl chlorosilane (1.1 g, 10.11 mmole) was added therein dropwise. Then, the resulting solution was stirred at 0-5° C. for 1.5 h, and the reaction was monitored by TLC (ethyl acetate:hexane=1:5). When there was no starting material observed, 0.5N of a sulfuric acid solution (5 mL) was added dropwise into the resulting solution, and the resulting solution was stirred at 0-5° C. for 2 hr and monitored by TLC (ethyl acetate:hexane=1:5). After ethyl acetate (200 mL) was added into the resulting solution, the organic layer was successively washed with a NaCl saturated solution (100 mL), a NaHCO$_3$ saturated solution (100 mL), water (2×100 mL) and a NaCl saturated solution (100 mL), dried over anhydrous sodium sulfate and concentrated to obtain a crude product of 31-trimethylsilylether Rapamycin (V-a) (2.758 g). The HPLC analysis data indicated that the crude product contained 94.5% (area %) of 31-trimethylsilylether Rapamycin (V-a) and 5.5% of Rapamycin (II).

Example 3

Preparation of 42-(dimethylphosphinate)-31-triethylsilylether Rapamycin (VI-b)

To a flask containing 31-triethylsilylether Rapamycin (V-b) (375 mg, 0.365 mmole) was added dichloromethane (3 mL) under a stream of N$_{2(g)}$. The resulting solution was stirred until 31-triethylsilylether Rapamycin (V-b) was completely dissolved and cooled to 0-5° C., and then a mixture of 2,6-di-tert-butyl-4-methylpyridine (165 mg, 1.096 mmole) and dichloromethane (1.5 mL) was added therein dropwise. Next, a mixture of dimethylphosphinic chloride (DMP-Cl) (173 mg, 1.461 mmole) and dichloromethane (0.5 mL) was added therein dropwise over a period of more than 10 min. The resulting solution was kept at 0-5° C. for 3 hr. To the resulting solution was added ethyl acetate (50 mL) dropwise, followed by ethyl acetate (150 mL). The resulting solution was successively washed with a NaHCO$_3$ saturated solution (50 mL) and a NaCl saturated solution (100 mL), then the organic layer was dried over anhydrous sodium sulfate and concentrated to obtain a crude product of 42-(dimethylphosphinate)-31-triethylsilylether Rapamycin (VI-b) (0.430 g). The yield thereof was 97.01%.

Example 4

Preparation of 42-(dimethylphosphinate)-31-triethylsilylether Rapamycin (VI-b)

To a flask containing 31-triethylsilylether Rapamycin (V-b) (200 mg, 0.194 mmole) was added dichloromethane (1 mL) under a stream of $N_{2(g)}$. The resulting solution was stirred until 31-triethylsilylether Rapamycin (V-b) was completely dissolved and cooled to 0-5° C., and then a mixture of 2,6-lutidine (46 mg, 0.428 mmole) and dichloromethane (0.5 mL) was added therein dropwise. Next, a mixture of dimethylphosphinic chloride (DMP-Cl) (92 mg, 0.778 mmole) and dichloromethane (0.5 mL) was added therein dropwise over a period of more than 10 min. The resulting solution was kept at 0-5° C. for 1.5 hr, and monitored with HPLC. To the resulting solution was added ethyl acetate (40 mL) dropwise, followed by ethyl acetate (360 mL). The resulting solution was successively washed with a NaHCO₃ saturated solution (100 mL), an iced HCl solution (0.5 N, 100 mL), a NaHCO₃ saturated solution (100 mL) and a NaCl saturated solution (100 mL), then the organic layer was dried over anhydrous sodium sulfate and concentrated to obtain a crude product containing 42-(dimethylphosphinate)-31-triethylsilylether Rapamycin (VI-b) and 31-triethylsilylether Rapamycin (V-b) (226 mg, and the ratio of (VI-b) to (V-b)=66.43:33.57).

Example 5

Preparation of 42-(dimethylphosphinate) Rapamycin (Ridaforolimus) (I) Using 31-trimethylsilylether Rapamycin (V-a) as a Starting Material To a flask containing 31-trimethylsilylether Rapamycin (V-a) (300 mg, 0.304 mmole) was added dichloromethane (2 mL) under a stream of $N_{2(g)}$. The resulting solution was stirred until 31-trimethylsilylether Rapamycin (V-a) was completely dissolved and cooled to 0-5° C. Next, a mixture of 3,5-lutidine (72 mg, 0.67 mmole) and dichloromethane (1 mL) was added therein dropwise over a period of more than 5 min. Then, a mixture of dimethylphosphinic chloride (DMP-Cl) (144 mg, 1.22 mmole) and dichloromethane (1 mL) was added therein dropwise over a period of more than 5 min. The resulting solution was kept at 0-5° C. for 1 hr, and monitored with HPLC. To the resulting solution was added ethyl acetate (40 mL) dropwise, followed by ethyl acetate until the final volume thereof was 300 mL. The resulting solution was successively washed with a NaHCO₃ saturated solution (100 mL), an iced HCl solution (0.5 N, 100 mL), a NaHCO₃ saturated solution (100 mL) and a NaCl saturated solution (100 mL), then the organic layer was dried over anhydrous sodium sulfate and concentrated to obtain a crude product of 42-(dimethylphosphinate) Rapamycin (Ridaforolimus) (I) (314 mg). The HPLC analysis data indicated that the crude product contained 81.03% (area %) of 42-(dimethylphosphinate) Rapamycin (Ridaforolimus) (I), 5.14% of Rapamycin (II), 0.54% of 31,42-bis(dimethyl phosphinate) Rapamycin (III), and 2.5% of 42-(dimethylphosphinate)-31-trimethylsilylether Rapamycin (VI-a).

Example 6

Preparation of 42-(dimethylphosphinate)-31-triethylsilylether Rapamycin (VI-b)

To a flask containing 31-triethylsilylether Rapamycin (V-b) (2.0 g, 1.945 mmole) was added dichloromethane (10 mL) under a stream of $N_{2(g)}$. The resulting solution was stirred until 31-triethylsilylether Rapamycin (V-b) was completely dissolved and cooled to 0-5° C. Next, a mixture of 3,5-lutidine (458 mg, 4.278 mmole) and dichloromethane (5 mL) was added therein dropwise over a period of more than 10 min. Then, a mixture of dimethylphosphinic chloride (DMP-Cl) (922 mg, 7.779 mmole) and dichloromethane (5 mL) was added therein dropwise over a period of more than 10 min. The resulting solution was kept at 0-5° C. for 1 hr, and monitored with HPLC. When there was no starting material observed, to the resulting solution was added ethyl acetate (50 mL) dropwise, followed by ethyl acetate (50 mL). The total organic layer was successively washed with a NaHCO₃ saturated solution (200 mL), an iced HCl solution (0.5 N, 200 mL), a NaHCO₃ saturated solution (200 in L) and a NaCl saturated solution (200 mL), dried over anhydrous sodium sulfate and concentrated to obtain a crude product of 42-(dimethylphosphinate)-31-triethylsilylether Rapamycin (VI-b) (2.312 g, purity=97.01%).

Example 7

Preparation of 42-(dimethylphosphinate) Rapamycin (Ridaforolimus) (I)

42-(dimethylphosphinate)-31-triethylsilylether Rapamycin (VI-b) (2.312 g, available from 1.945 mmole of Rapamycin-28-triethylsilylether) and tetrahydrofuran (60 mL) was placed into a flask, and the resulting solution was cooled to 0~-5° C. Next, a sulfuric acid solution (2 N, 6 mL) was slowly added into the resulting solution dropwise. When the 42-(dimethylphosphinate)-31-triethylsilylether Rapamycin (VI-b) was less than 2%, ethyl acetate (1000 mL) was added into the resulting solution. Then, the organic layer was successively washed with a NaCl saturated solution (300 mL), a NaHCO₃ saturated solution (200 mL) and a NaCl saturated solution (200 mL), dried over anhydrous sodium sulfate and concentrated to obtain a crude product of 42-(dimethylphosphinate) Rapamycin (Ridaforolimus) (I) (2.341 g). The crude product was then purified by Licrhoprep RP-18 silica gel chromatography (eluted with acetonitrile: 0.02 M ammonium formate solution=6:4, wherein the pH of the ammonium formate solution was adjusted to 4.0 with formic acid), extracted with ethyl acetate, concentrated and dried to obtain a white foam solid 42-(dimethylphosphinate) Rapamycin (Ridaforolimus) (I) (1.840 g, purity=99.48%). The yield thereof was 95.55% based on 2.0 g of 31-triethylsilyl ether Rapamycin.

$^1$H-NMR (400 MHz, CDCl₃) δ 4.18 (m, 1H), 4.10 (m, 1H), 3.05 (m, 1H), 1.51 (m, 6H); $^{31}$P-NMR (161 MHz, CDCl₃) δ 53.33; 1012.6 m/z [M+Na]⁺.

Although the present invention has been explained in relation to its preferred embodiment, it is to be understood that many other possible modifications and variations can be made without departing from the spirit and scope of the invention as hereinafter claimed.

What is claimed is:

1. A method for preparing 42-(dimethylphosphinate) Rapamycin (Ridaforolimus) of the following formula I, comprising the following steps:

I

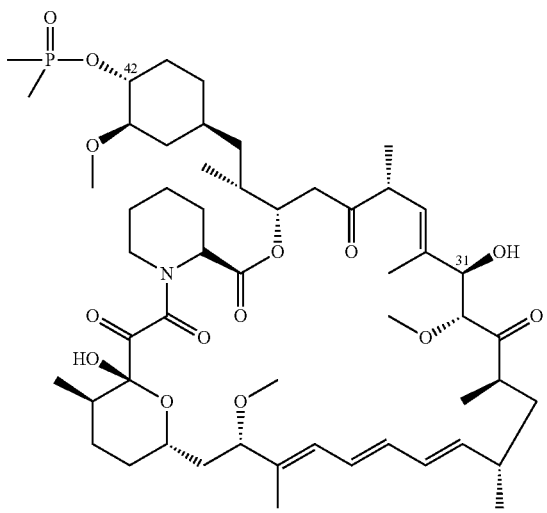

(a) reacting Rapamycin of the following formula II with a silane compound in a first basic condition to obtain a compound of the following formula IV:

II

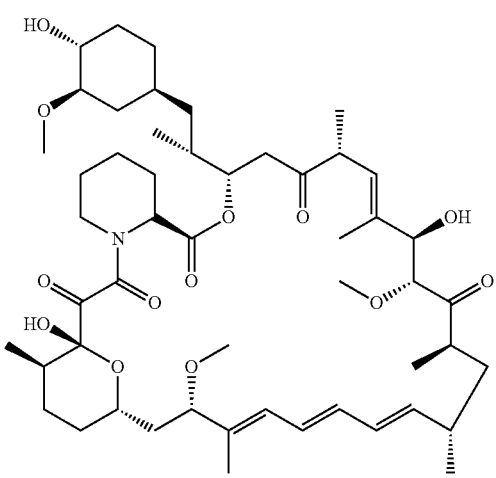

IV

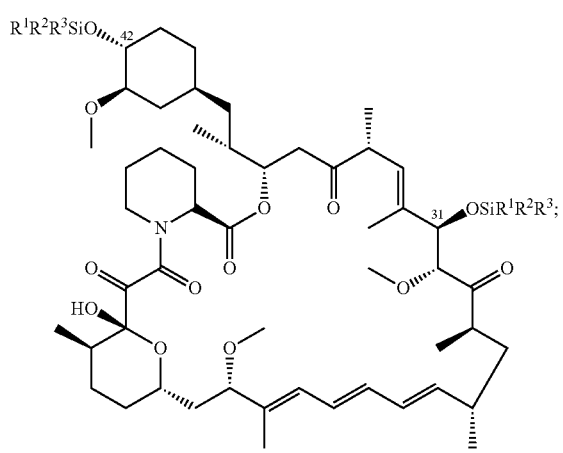

(b) deprotecting the compound of the formula IV in a first acid condition to obtain a compound of the following formula V:

V

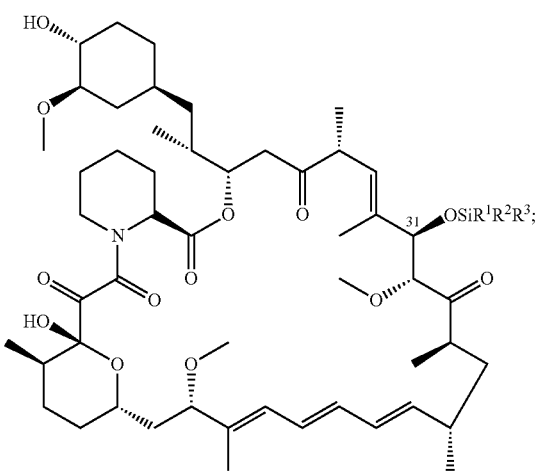

(c) reacting the compound of the formula V with Dimethylphosphinic chloride in a second basic condition to perform a phosphorylation reaction to obtain a compound of the following formula VI:

VI

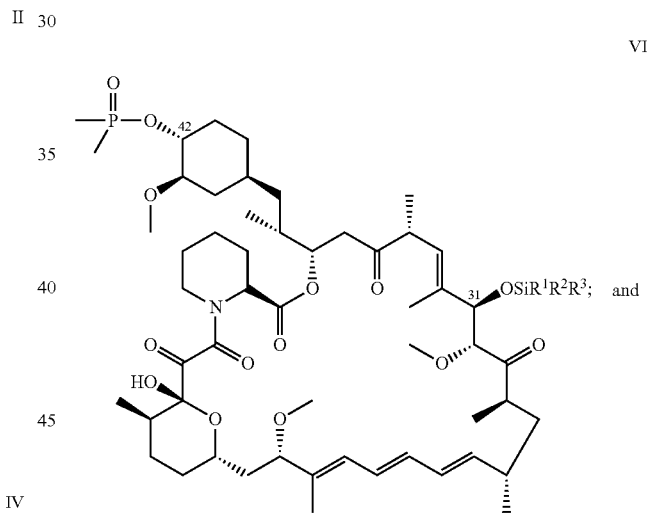
and (d) hydrolyzing the compound of the formula VI in a second acid condition to obtain Ridaforolimus of the formula I,
wherein each $R^1$, $R^2$ and $R^3$ is independently H, $C_{1-6}$ linear alkyl, benzyl, phenyl, or p-methylbenzyl, with the proviso that all $R^1$, $R^2$ and $R^3$ are not H.

2. The method as claimed in claim 1, wherein the silane compound used in the step (b) is represented by the following formula VII:

VII

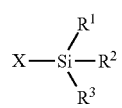

wherein each $R^1$, $R^2$ and $R^3$ is independently H, $C_{1-6}$ linear alkyl, benzyl, phenyl, or p-methylbenzyl, with the proviso that all $R^1$, $R^2$ and $R^3$ are not H, and X is Cl or $-OSO_2CFF_3$.

3. The method as claimed in claim 1, wherein an acid used in the first acid condition of the step (b) is hydrogen chloride, acetic acid, sulfuric acid, trifluoroacetic acid, hydrofluoric acid, or a combination thereof.

4. The method as claimed in claim 1, wherein a base used in the second basic condition of the step (c) is 2,6-di-tert-butyl-4-methylpyridine, 3,5-lutidine, 2,6-lutidine, 2,4-lutidine, 2,3-lutidine, 2,5-lutidine, 3,4-lutidine, pyridine, 4-dimethylaminopyridine (DMAP), or a combination thereof.

5. The method as claimed in claim 1, wherein an acid used in the second acid condition of the step (d) is hydrogen chloride, acetic acid, sulfuric acid, tetrabutylammonium fluoride, trifluoroacetic acid, hydrofluoric acid, or a combination thereof.

6. The method as claimed in claim 3, wherein a solvent used in the first acid condition of the step (b) is at least one selected from the group consisting of tetrahydrofuran, dichloromethane, acetonitrile, ethyl acetate, dimethylformamide, and water.

7. The method as claimed in claim 4, wherein a solvent used in the second basic condition of the step (c) is at least one selected from the group consisting of tetrahydrofuran, dichloromethane, acetonitrile, and dimethylformamide.

8. The method as claimed in claim 5, wherein a solvent used in the second acid condition of the step (d) is at least one selected from the group consisting of tetrahydrofuran, dichloromethane, acetonitrile, ethyl acetate, dimethylformamide, and water.

\* \* \* \* \*